United States Patent [19]

Fritz et al.

[11] Patent Number: 4,745,177
[45] Date of Patent: May 17, 1988

[54] DESULFATOHIRUDINS, THE PREPARATION THEREOF AND PHARMACEUTICAL COMPOSITIONS CONTAINING THEM

[75] Inventors: Hans Fritz, Hoenbrunn; Johannes Dodt; Ursula Seemüller, both of Munich; Ernst Fink, Westerstede-Giesselhorst, all of Fed. Rep. of Germany

[73] Assignees: Ciba-Geigy Corporation, Ardsley, N.Y.; Plantorgan Werk Heinrich G.E. Christensen KG, Bad Zwischenahn, Fed. Rep. of Germany

[21] Appl. No.: 929,710

[22] Filed: Nov. 13, 1986

Related U.S. Application Data

[62] Division of Ser. No. 673,952, Nov. 21, 1984, Pat. No. 4,654,302.

[30] Foreign Application Priority Data

Nov. 22, 1983 [DE] Fed. Rep. of Germany ....... 3342139

[51] Int. Cl.$^4$ .................. C07K 7/10; A61K 37/43; A61K 37/02
[52] U.S. Cl. ...................................... 530/324; 514/12
[58] Field of Search .......................... 530/324; 514/12

[56] References Cited

U.S. PATENT DOCUMENTS 4,668,662 5/1987 Tripier ............................. 514/12

OTHER PUBLICATIONS

Dodt et al., FEBS Lett, vol. 165, No. 2, pp. 180–184 (Jan. 1984).
Walsmann et al, Die Pharmazie, 36: pp. 653–660 (1981).
P. D. Boyer, The Enzymes, 3rd Ed. Academic Press, New York, vol. 5, pp. 21–41 (1971).

Primary Examiner—Lionel M. Shapiro
Attorney, Agent, or Firm—Michael W. Glynn; Irving M. Fishman; Norbert Gruenfeld

[57] ABSTRACT

The present invention relates to desulfatohirudins, to the preparation thereof, to pharmaceutical compositions containing these compounds, and to the use thereof.

The desulfatohirudins of this invention correspond to hirudin in biological activity and are therefore particularly useful for inhibiting blood clotting.

4 Claims, No Drawings

DESULFATOHIRUDINS, THE PREPARATION THEREOF AND PHARMACEUTICAL COMPOSITIONS CONTAINING THEM

This is a division of application Ser. No. 673,952 filed on Nov. 21, 1984.

The present invention relates to novel biologically active polypeptides derived from hirudin, to the preparation thereof, to pharmaceutical compositions containing the novel compounds and to their use, in particular for inhibiting blood coagulation.

Hirudin, from which the compounds of this invention are derived, is a naturally occurring polypeptide which is produced in the organism of medicinal leeches (Hirudo medicinalis) and which keeps the blood ingested by the leech from coagulating. Its isolation, purification, chemical composition as well as its broad biological and medicinal use as anticoagulant are known and have been summarised and discussed in detail in articles, for example, by P. Walsmann and F. Markwardt, Pharmazie 36, 653–660 (1981). Recently, the complete amino acid sequence of hirudin was finally elucidated, thereby creating the first theoretical basis for experiments to synthesise it. The primary structure of hirudin conforms to the formula:

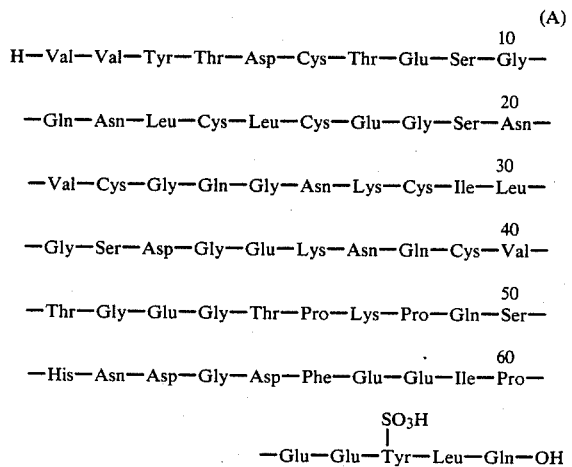

(Which specific cystein residues are linked together in pairs by disulfide bridges still remains to be determined; however, this structural detail is of minor importance for the plan of synthesis). The structure is distinguished by a characteristic accumulation of hydrophobic amino acids towards the amino terminal and of polar amino acids towards the carboxyl terminal of the peptide and also, as a special feature, by the strongly acidic sulfuric acid monoester group at the phenolic hydroxyl group of the tyrosine residue in position 63, corresponding to the partial formula

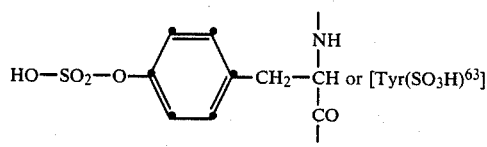

Up to now there have been no clear ideas on the biological function of the sulfate group in proteins quite generally and in this compound in particular. The following hypotheses have been discussed:

(1) a significance for the biological properties of the protein;

(2) a participation in regulatory cell processes (in a manner similar to that known for reversible phosphorylation);

(3) a stimulation of secretion, i.e. the sulfation acts as marker for identification as secretory protein: all sulfated proteins discovered up to now are secretory or transmembranal proteins. At all events, the sulfate group is one of the most striking structural features of hirudin.

Hirudin is one of the most potent thrombin inhibitors known and has a $K_i$ value of about $6.10^{-11}M$. It is completely specific for thrombin and does not inhibit other proteinases of the clotting cascade. In contrast to heparin, hirudin has a direct inhibiting action on thrombin and not through antithrombin III. The only pharmacological effect observed of purified hirudin is that of anticoagulation and of thrombosis prophylaxis. No effect on heart rate, resipiration, blood pressure, thrombocytes, fibrinogen and haemoglobin is observed when unusually high doses are given to dogs. In tests on rats, pigs, and dogs, hirudin has proved effective in experimental thrombosis (induced either by stasis or by thrombin injection), in endotoxin shock as well as in DIC (disseminated intravascular coagulation). Whenever direct comparison tests were carried out, hirudin proved superior to heparin.

Although long known, hirudin has not so far achieved the broad therapeutic use which one would be entitled to expect from its excellent biological properties. The grave drawback of its extremely limited accessibility stands in the way of its widespread use in medicine. Up to now, hirudin preparations have been obtained exclusively from natural material which is expensive and difficult of access—medicinal leeches—by complicated isolation and purification procedures. The relatively long sequence of 65 amino acids affords little hope of practical success of an approach by conventional peptide synthesis. Just as unpromising, however, was the alternative route of biosynthesis, which could be accomplished by synthesing a suitable polynucleotide and inserting it into the genetic code of a production micro-organism in accordance with the general methods of gene manipulation. It was to be expected that the necessary introduction of the O-sulfonated tyrosine residue would give rise to almost insuperable difficulties in a direct biosynthesis.

Surprisingly, it has now been found that, contrary to the above theoretical conceptions, the favourable biological properties of hirudin are also retained if the characteristic sulfuric acid monoester group is removed from the phenolic hydroxyl group of the [Tyr$^{63}$] residue. Except for the absence of the sulfate group at the Tyr$^{63}$ residue, both resultant degradation products, i.e. the desulfatohirudins of the formulae I and II, are characterised by all other structural features of hirudin, with the unshortened amino acid sequence being present in the desulfatohirudin of the formula I, which is the actual desulfatohirudin in the narrow sense of the term, whereas the analogous hexacontatripeptide, designated as desulfatohirudin of the formula II, which is equivalent in potency, additionally lacks the two C-terminal amino acids Leu and Gly. Surprisingly, however, these compounds are, both qualitatively and quantitatively, at least equivalent to hirudin in their anti-coagulative properties.

This is of great importance with respect to the possibilities of a conventional biotechnological synthesis of this peptide. Whereas the presence of the unusual hydroxysulfonyl group in hirudin virtually rules out direct biosynthesis, the absence of this group in desulfatohirudin provides substantially better structural conditions for a successful biotechnological synthesis. Given the equivalence of its biological activity, desulfatohirudin is clearly superior to hirudin technically and economically on account of its substantially better accessibility by the biotechnological route.

In the practice of this invention, the desulfatohirudins of formulae I and II can be obtained in a manner known per se. Thus, for example, they can be prepared by setting free the phenolic hydroxyl group of the tyrosine residue in position 63, which is present in sulfated form, in the hexacontapentapeptide hirudin of formula A as indicated above.

The process for setting free this group in accordance with the scheme

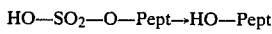

(wherein Pept is the residual part of hirudin), can be effected in a manner known per se, e.g. by hydrolysis employing either chemical or biological methods.

A chemical process to effect this liberation is preferably carried out under the general conditions of acid-catalysed hydrolysis with a dilute, e.g. about 2 to 4N, aqueous solution of hydrochloric acid, advantageously in trifluoroacetic acid as reaction medium, or with aqueous trifluoroacetic acid alone as both reactant and solvent. In order to keep to a minimum the danger of hydrolytic splitting of peptide bonds, it is advisable to carry out the reaction under mild conditions, e.g. in a temperature range not exceeding room temperature, and to follow the course of the hydrolysis analytically, e.g. by thin-layer chromatography.

In particular, however, the hydrolysis is carried out by biological means, preferably by using specific enzymes, namely arylsulfatases which cleave the phenolic sulfate ester groups to free phenolic groups under mild conditions. The biological cleavage of the sulfated hydroxyl group can be effected with the aid of a suitable enzyme preparation with enriched active componentt or of an isolated enzyme; or else a suitable enzyme system can be employed in situ, i.e. one that is directly present in a living or dead biological material, for example a growing or quiescent micro-organism, a cell culture, a cell homogenate or an autolysate. One of the great advantages of biological hydrolysis is its high selectivity which effects only the desired splitting of the monosulfuric acid ester bond without attacking the other functional groups, in particular the peptide bonds, in the sensitive starting material. In particular, the compounds of the invention are obtained by treating hirudin in an aqueous, preferably buffered, solution or suspension with an individual arylsulfatase preparation, e.g. the arylsufatase of Helix pomatia, at a temperature normally employed for enzymatic processes, for example in the range from about 20° to 45° C. and preferably from 25° to 30° C. A weakly acid reaction is preferred, i.e. at a pH of about 4 to 7, in particular from about 5 to 6, which value is adjusted with a buffer such as an approximately 0.03 to 0.3 molar solution of a salt of an organic carboxylic acid with an alkali metal or with an organic base, e.g. with sodium acetate or, preferably, pyridine acetate (of about pH 5.4). The ratio of enzyme employed to the substrate (hirudin) depends in general on the activity of the respective preparation and is usually from about 1:1 to 1:100, preferably from about 1:5 to 1:20. It is advantageous to use enzymes of the greatest possible purity and activity. As the arylsulfatase catalyses not only the removal but also the introduction of the sulfate group and effects the adjustment of an equilibrium between starting materials and final products, it is advantageous to determine by preliminary experiments, for each enzyme preparation, the optimum concentration, the ratio to the substrate, and the time required for the desulfation. As a rule, the reaction is complete after a few minutes. However, the quality of the reaction product is not impaired even on longer contact (up to about 4 hours) with the active enzyme (e.g. when the reaction mixture is allowed to stand).

The course of the enzymic desulfation can be followed by bioanalysis of samples taken from the reaction mixture. The procedure is, for example, that the enzyme activity is destroyed by heating the sample briefly (for about 3 minutes) to about 100° C., and the substrate is treated with a carboxypeptidase Y. (The carboxypeptidase Y degrades the peptide chain starting at the carboxyl terminal, whereas the amino acids are split off successively by cleaving the respective amide bonds). As a rule, the degradation of the peptide chain is so far advanced after about 15 minutes that the sulfated and/or free amino acid in position 63 (Tyr$^{63}$) is completely split off and is thus made available for determination in a conventional amino acid analyser.

The desulfatohirudin of the formula II is formed by splitting off both C-terminal amino acid components Leu and Gly during the hydrolysis of hirudin. The separation of the components of the mixture so obtained can be followed for example by preparative chromatography. The desulfatohirudin of the formula II has the same biological properties as the desulfatohirudin of the formula I.

The desulfatohirudins of this invention can be not only in the free form but also in the form of their salts. As they contain free amino and amidino groups in several amino acid residues, the compounds of the invention can be in the form of acid addition salts. Suitable acid addition salts are in particular physiologically tolerable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid and stearic acid, malic acid, tartaric acid, ascorbic acid and citric acid. As, however, the desulfatohirudins also contain free carboxyl groups in several amino acid residues, which carboxyl groups impart acidic character to the entire peptide, they can also be in the form of salts, e.g. sodium, potassium, calcium or magnesium salts, or also as ammonium salts derived from ammonia or a physiologically tolerable organic nitrogen-containing base. However, as they contain at the same time free carboxyl groups and free amino (amidino) groups, they can also be in the form of inner salts.

Depending on the method employed, the compounds of the formula I are obtained in the free form or in the form of acid addition salts, inner salts or salts with bases. The free compound can be obtained in known manner from the acid addition salts. In turn, therapeutically acceptable acid addition salts can be obtained from the free compounds by reaction with acids, e.g. with those acids which form the above-mentioned salts, and by evaporation or lyophilisation. The inner salts can be obtained by adjusting the pH to a suitable neutral point.

The invention also relates to pharmaceutical compositions which contain at least one of the compounds of the invention or a pharmaceutically acceptable salt thereof, optionally together with a pharmaceutical carrier and/or excipient.

These compositions can be used in particular for the above indications by e.g. parenteral (such as intravenous, intracutaneous, intramuscular or subcutaneous) or oral administration or by topical application. The dosage depends primarily on the specific formulation and on the object of the therapy or prophylaxis. The amount of the individual doses as well as the mode of administration is best determined by individually assessing the particular case. The appropriate methods of determining relevant blood factors are known to the skilled person.

For injection, the therapeutic amount of the compounds of this invention will normally be in the dosage range from about 0.005 to 0.1 mg/kg of body weight, with the range from about 0.01 to 0.05 mg/kg of body weight being preferred. Administration is made by intravenous, intramuscular or subcutaneous injection. Accordingly, pharmaceutical compositions for parenteral administration will contain, in single dosage unit form, depending on the mode of administration, about 0.4 to 7.5 mg of compound of the invention per dose. In addition to the active ingredient, these pharmaceutical compositions will usually contain a buffer, e.g. a phosphate buffer which keeps the pH in the range from about 3.5 to 7, and also sodium chloride, mannitol or sorbitol for adjusting the isotonic pressure. The compositions can be in the form of lyophilisates or solutions. Solutions can contain with advantage a microbicidal preservative, e.g. 0.2 to 0.3% of methyl or ethyl 4-hydroxybenzoate.

A composition for topical application can be formulated as an aqueous solution, lotion or jelly, an oily solution or suspension, or as a fatty, in particular, emulsified ointment. A composition in the form of an aqueous solution is obtained for example by dissolving a compound of the invention, or a therapeutically acceptable salt thereof, in an aqueous buffer solution of pH 4 to 6.5 and, if desired, adding a further active ingredient, e.g. an anti-inflammatory agent, and/or a polymeric binder, e.g. polyvinylpyrrolidone, and/or a preservative. The concentration of active ingredient is from about 0.08 to 1.5 mg, preferably from 0.25 to 1.0 mg, in about 10 ml of a solution or 10 g of a jelly.

An oily formulation for topical application is obtained for example by suspending a compound of the invention, or a therapeutically acceptable salt thereof, in an oil, optionally with the addition of a swelling agent such as aluminium stearate, and/or a surfactant having an HLB value (hydrophilic-lipophilic balance) below 10, for example a fatty acid monoester of a polyhydric alcohol, e.g. glycerol monostearate, sorbiton monolaurate, sorbitan monostearate or sorbitan monooleate. A fatty ointment is obtained for example by suspending a compound of the invention, or a therapeutically acceptable salt thereof, in a spreadable fatty base, optionally with the addition of a surfactant having an HLB value below 10. An emulsified ointment is obtained by triturating an aqueous solution of a compound of the invention, or a salt thereof, in a soft, spreadable fatty base with the addition of a surfactant having an HLV value below 10. All these formulations for topical application can also contain preservatives. The concentration of active ingredient is about 0.08 to 1.5 mg, preferably 0.25 to 1.0 mg, in about 10 g of base.

In addition to the above and to analogous pharmaceutical compositions which are intended for medicinal use in or on the human or animal body, the present invention also relates to pharmaceutical compositions and preparations for medicinal use outside the living body of humans or animals. Such compositions or preparations are used in particular as anticoagulants for blood which is subjected to extracorporeal circulation or treatment (e.g. renal dialysis), preservation or modification (e.g. haemoseparation). Such preparations are similar in composition and are for example stock solutions or also formulations in single dosage unit form similar to the above described injection preparations. However, the amount or concentration of active ingredient is conveniently based on the volume of the blood to be treated or, more precisely, to the thrombin content. In this connection it must be ensured that the compounds of the invention (in the free form)

(a) completely deactivate about 5 times the amount by weight of thrombin;

(b) are physiologically harmless even in larger amounts; and (c) are eliminated from the blood very rapidly even in large concentrations so that there is no danger of overdosage, even e.g. during transfusions. Depending on the specific purpose, the suitable dose is from about 0.01 to 1.0 mg of the active ingredient per liter of blood, although the upper limit may be considerably exceeded without danger.

The present invention also relates to the bioanalytical use of the compounds of the invention and salts thereof for thrombin determination and to the preparations for this purpose which contain the compounds of the invention, for example mixtures of solids and preferably solutions, in particular aqueous solutions. In addition to an exact amount or concentration of compounds of the invention (also in salt form), these preparations can conveniently also contain inert excipients, e.g. those mentioned above in connection with injection preparations, which act for example as stabilisers and/or preservatives. These preparations are used for bioanalysis in similar known manner as the hirudin compositions, for example for thrombin determination.

Throughout this specification and in the claims, the abbreviations employed for amino acids and their residues are used in conformity with the generally accepted rules of nomenclature and relate to α-amino acids and their residues of the L-series.

The invention is illustrated by the following Examples.

EXAMPLE 1

Material: Hirudin, activity 630 IU/mg

The biological activity is determined from the inhibition of thrombin, whose enzymatic activity is in turn determined using the chromogenic substrate Chromozym TH (a product of Boehringer, Mannheim, West Germany, for thrombin and hirudin determination) in accordance with known directions supplied with the test preparation.

Arylsulfatase (ARS) from Helix pomatia (a product of Boehringer, Mannheim, West Germany), 5 IU/mg.

The enzymatic activity is determined by the known method of Leon et al., Biochem. J. 75, 612–617, using the chromogenic substrate p-nitrophenol sulfate (1.8 mM/l in the batch).

Desulfation (1) Preliminary experiment (for determining the optimum ARS concentration)

(a) the following stock solutions are prepared:

(A) Hirudin solution having a concentration of 2 mg/ml, obtained by dissolving hirudin in solution (C).

(B) Arylsulfatase solution with a concentration of 1.25 mg/ml: by mixing 25 parts of the commercially available suspension with 100 parts of solution (C).

(C) Buffer solution: 0.1M aqueous solution of pyridine acetate, pH 5.4.

(b) Procedure

A series of samples is obtained by mixing the following components: each sample contains 15 $\mu$l of solution A (corresponding to 30 $\mu$g of hirudin) and 10 $\mu$l of solution B (corresponding to 12.5 $\mu$g of arylsulfatase) or of a solution in which the concentration of the enzyme is adjusted to ½, ¼, ⅛, 1/16 and 1/32 of the original concentration by diluting solution B with the buffer C. Each sample of 25 $\mu$l is incubated for 60 minutes at 25° C., then heated for 3 minutes to 100° C. to denature the sulfatase, rapidly cooled, and analysed for content of free and sulfated tyrosine (in accordance with the method described below).

(2) Preparatory process 15 parts by volume of solution A are mixed with 10 parts by volume of a dilute solution B, whose optimum lowest possible concentration of each solution was determined in the preliminary experiment and adjusted by diluting stock solution B with the buffer solution C. The mixture is incubated at 25° C. for about 30–60 minutes, heated briefly (e.g. under conditions of flash sterilisation) to 100° C. and immediately cooled in order to denature the desulfating enzyme. The reaction mixture is separated through a column of Sephadex ® G50 or G75, CM-Sephadex ®, Wofatit ® CP, Amberlite ® IRC or another equivalent cation exchanger, if desired after concentrating the reaction mixture in vacuo at or below room temperature. If required, this separation is repeated until desulfatohirudin of the desired purity (determined e.g. by the inhibitory test with thrombin and/or amino acid analysis, q.v. below) is obtained. The product in solid form is obtained by lyophilising the corresponding solutions (eluates).

According to the amino acid analysis (by C-terminal proteolysis), the pure product should be free from tyrosine O-sulfate and exhibit the full activity of hirudin in the inhibitory activity test on thrombin (e.g. with Chromozym TH, q.v. above).

Analytical control of the desulfation is made by successive proteolytic degradation of the carboxyl terminal portion of hirudin (as starting material), samples of the desulfation process and desulfatohirudin of the formula I (as final product) with carboxypeptidase Y, and by quantitative determination of the liberated amino acid residues by means of a conventional amino acid analyser.

(a) The following stock solutions are prepared:

(Aa) Hirudin solution with a concentration of 0.806 mg/ml is obtained by dissolving 0.250 parts by weight of hirudin in 310 parts by volume of buffer solution Ca (q.v. below).

(Ba) CPY solution with a concentration of 2 mg/ml is obtained by dissolving 2 parts by weight of carboxypeptidase Y (CPY) in 1000 parts by volume of buffer solution Ca.

(Ca) Buffer solution: 0.1M aqueous solution of pyridine acetate, pH 5.4.

(b) Procedure

275 $\mu$l of solution Aa, corresponding to 222 $\mu$g of hirudin, are mixed with 8 $\mu$l of solution Ba, corresponding to 16 $\mu$g of CPY, i.e. in a ratio to hirudin of 1:4 (weight/weight) or 1:125 (mole/mole), and the mixture is incubated for 30 minutes at 25° C. A 30 $\mu$l sample is taken from the mixture, 5 $\mu$l of trifluoroacetic acid are added and the batch is centrifuged to remove the CPY precipitate of CPY. The supernatant solution is evaporated to dryness and the amino acids present in the residue are taken up in a buffer solution intended for the amino acid analysis amd determined quantiatively with the aid of a conventional amino acid analyser. Desulfatohirudin of the formula I is also analysed in the same manner. (The result can also be expressed as molar ratio of the amino acids, in particular of the tyrosine O-sulfate or free tyrosine to hirudin). For control samples, hirudin and CPY are each subjected alone to the same procedure.

In the same manner, 25 $\mu$l samples taken from the preliminary desulfation preliminary experiment after destroying ARS activity by brief heating are each mixed with 2 $\mu$g of CPY (in the form of solution Ba) and the mixtures are incubated for 30 minutes at 25° C. After addition of 5 $\mu$l of of trifluoroacetic acid, centrifugation and lyophilisation of the supernatant, liberated amino acids are determined quantitatively in an analyser. (Control runs are individually carried out with: (1) hirudin, (2) CPY, (3) ARS, (4) hirudin+CPY, (5) hirudin+ARS, (6) CPY+ARS).

EXAMPLE 2

Material:

Hirudin: 1.5 mg of hirudin (purified with HLPC)

Arylsulfatase (from Helix pomatia) in suspension (a product obtained from Boehringer): 5 mg/ml=5 IU/mg.

The arylsulfatase (ARS) is desalted through a PD 10 column before the experiment. 100 $\mu$l suspensions are made up to 2.5 ml of buffer (0.1M NH$_4$Ac, pH 5.5), added to the column and eluted with 3 ml of buffer. The extinction of the eluted solution is $E_{280}=0.139$; 100 $\mu$l of the solution correspond to 16 $\mu$g of ARS.

Method

Hirudin is dissolved in 2 $\mu$g/$\mu$l of buffer (0.1M NH$_4$Ac, pH 5.5). To 20 $\mu$g of hirudin (=10 $\mu$l) are added 100 $\mu$l of the ARS solution in buffer.

Weight ratio of enzyme (ARS):substrate (hirudin)=1:1.25.

A batch on a preparative scale is run for 22 hours at 25° C. The reaction course is followed by HPLC analysis using 2.7 $\mu$g of inhibitor for each determination.

After 6 hours, the hirudin is 90% desulfated to the desulfatohirudin of the formula (I). After 22 hours, a mixture of the desulfatohirudin of the formula (I) and the desulfatohydrin of the formula (II) is obtained (I:II=55:45). This mixture can be separated by the chromatographic method described in Example 1.

The protein-chemical characterisation of the final products is made by the dansyl chloride method (N-terminal determination), by degradation with carboxypeptidase Y (C-terminal determination) and by amino acid analysis over 24 and 48 hours.

What is claimed is:

1. A desulfatohirudin of the formula I $$
\begin{aligned}
&\text{H—Val—Val—Tyr—Thr—Asp—Cys—Thr—Glu—Ser—Gly—} \\
&\text{—Gln—Asn—Leu—Cys—Leu—Cys—Glu—Gly—Ser—Asn—} \\
&\text{—Val—Cys—Gly—Gln—Gly—Asn—Lys—Cys—Ile—Leu—} \\
&\text{—Gly—Ser—Asp—Gly—Glu—Lys—Asn—Gln—Cys—Val—} \\
&\text{—Thr—Gly—Glu—Gly—Thr—Pro—Lys—Pro—Gln—Ser—} \\
&\text{—His—Asn—Asp—Gly—Asp—Phe—Glu—Glu—Ile—Pro—} \\
&\text{—Glu—Glu—Tyr—Leu—Gln—OH}
\end{aligned} \quad (I)
$$

or of the formula II $$
\begin{aligned}
&\text{H—Val—Val—Tyr—Thr—Asp—Cys—Thr—Glu—Ser—Gly—} \\
&\text{—Gln—Asn—Leu—Cys—Leu—Cys—Glu—Gly—Ser—Asn—} \\
&\text{—Val—Cys—Gly—Gln—Gly—Asn—Lys—Cys—Ile—Leu—} \\
&\text{—Gly—Ser—Asp—Gly—Glu—Lys—Asn—Gln—Cys—Val—} \\
&\text{—Thr—Gly—Glu—Gly—Thr—Pro—Lys—Pro—Gln—Ser—} \\
&\text{—His—Asn—Asp—Gly—Asp—Phe—Glu—Glu—Ile—Pro—} \\
&\text{—Glu—Glu—Tyr—OH}
\end{aligned} \quad (II)
$$

wherein the —Cys— residues are linked in pairs by disulfide bridges in the same manner as in hirudin, or a salt thereof.

2. The desulfatohirudin according to claim 1 characterised by formula I, or a pharmaceutically acceptable salt thereof.

3. The desulfatohirudin according to claim 1 characterised by formula II, or a pharmaceutically acceptable salt thereof.

4. A pharmaceutical composition containing at least one desulfatohirudin according to claim 1, or a pharmacologicallly acceptable salt thereof, optionally together with at least one pharmaceutical carrier or excipient.

* * * * *